(12) United States Patent
Block

(10) Patent No.: US 6,992,772 B2
(45) Date of Patent: Jan. 31, 2006

(54) METHOD AND APPARATUS FOR OPTICAL SAMPLING TO REDUCE INTERFERING VARIANCES

(75) Inventor: Myron J. Block, Jupiter Island, FL (US)

(73) Assignee: Optix LP, Jupiter, FL (US)

(*) Notice: Subject to any disclaimer, the term of this patent is extended or adjusted under 35 U.S.C. 154(b) by 52 days.

(21) Appl. No.: 10/601,254

(22) Filed: Jun. 19, 2003

(65) Prior Publication Data

US 2004/0257557 A1    Dec. 23, 2004

(51) Int. Cl.
G01N 21/55    (2006.01)

(52) U.S. Cl. .................... 356/445; 600/323
(58) Field of Classification Search .............. 356/32, 356/445–448; 600/310, 322–324, 334–344
See application file for complete search history.

(56) References Cited

U.S. PATENT DOCUMENTS

| | | | |
|---|---|---|---|
| 4,013,067 A * | 3/1977 | Kresse et al. ............... 600/479 |
| 4,013,784 A | 3/1977 | Kresse | |
| 4,655,225 A | 4/1987 | Dähne et al. | |
| 5,285,784 A * | 2/1994 | Seeker ........................ 600/331 |
| 5,321,265 A | 6/1994 | Block | |
| 5,424,545 A | 6/1995 | Block et al. | |
| 5,434,412 A | 7/1995 | Sodickson et al. | |
| 5,452,717 A * | 9/1995 | Branigan et al. ........... 600/323 |
| 5,672,875 A | 9/1997 | Block et al. | |
| 5,818,044 A | 10/1998 | Sodickson et al. | |
| 5,818,048 A | 10/1998 | Sodickson et al. | |
| 6,028,311 A | 2/2000 | Sodickson et al. | |
| 6,343,223 B1 * | 1/2002 | Chin et al. .................. 600/323 |
| 6,411,832 B1 | 6/2002 | Guthermann | |
| 6,420,709 B1 | 7/2002 | Block et al. | |
| 6,442,411 B1 | 8/2002 | Guthermann | |

OTHER PUBLICATIONS

International Search Report for PCT/US04/18984.

* cited by examiner

*Primary Examiner*—Michael P. Stafira
(74) *Attorney, Agent, or Firm*—Ralph Loren; Palmer & Dodge LLP

(57) ABSTRACT

The present invention relates to a method and apparatus of that utilizes a reflective enclosure to simulate optical homogeneity in an otherwise inhomogeneous sample. The illumination sources and sample are placed within the reflective enclosure, thus providing a method for examining a sample that is different from transmission, reflection or transflection. This apparatus and method are particularly well adapted to in vivo non-invasive testing for constituents of blood.

30 Claims, 2 Drawing Sheets

METHOD AND APPARATUS FOR OPTICAL SAMPLING TO REDUCE INTERFERING VARIANCES

BACKGROUND OF THE INVENTION

In a number of circumstances, e.g., taking non-invasive in vivo measurements, the sample is inhomogeneous. Because of this inhomogeneity, errors are often introduced into the measurement process. In vivo non-invasive measurements of substances such as glucose or hemoglobin using optical systems are particularly susceptible to this problem. Measurement through a finger can have problems with variations of pathlength, variations of water content, density differences along with pathlength, shunting of signal, relative motion of sources and detectors and a host of other problems. To ameliorate these problems, a variety of techniques have been attempted. For example, in pulse oximetry, spring loaded clamps or adhesive tape are used to hold the source and detector system to the finger. This clamping eliminates some of the problems of relative motion but does not cure other sources of variance. In fact, clamping of the finger or earlobe to make non-invasive measurements can cause new problems by deformation of the tissue in an inconsistent and irreproducible way.

U.S. Pat. Nos. 5,424,545 and 5,434,412, both issued on applications of Block and Sodickson, the disclosures of which are incorporated herein by reference, are directed to different methods of attempting to cure the problems caused by inhomogeneity of the sample. In these patents, congruent sampling is used to try to minimize the difference in pathlength from the light source to the detector. These patents use optical systems which make either the light sources or detectors (or both) optically congruent; that is, the detectors view the same portion of the sample and source through the same solid angle and at the same distance. While these systems provide a benefit in reducing several of the sources of the inaccuracy caused by an inhomogeneous sample, particularly those associated with differences in pathlength, they cannot solve all of the problems. In addition, because of the need for prisms and other optical components to make the pathlengths equal, these systems are inherently bulky.

Another approach to dealing with some of the problems in output caused by the inhomogeneity of the sample is shown in the Dähne, U.S. Pat. No. 4,655,225, the disclosure of which is incorporated herein by reference. This patent uses an integrating sphere to capture light exiting a finger without regard to the directional aspect. The input port of the integrating sphere is placed next to the finger so that all of the light transmitted through the finger enters the integrating sphere and is captured so as to increase signal. A problem with this type of apparatus is that it also allows any light that is shunted (e.g., light that does not go through the area of interest) to be collected as well. In addition, because the light used to illuminate the finger may illuminate areas that have inhomogeneities, thus causing scattering, the use of the integrating sphere as shown in the Dähne patent captures light from these inhomogeneous areas as well.

U.S. Pat. No. 5,672,875, also on an application of Block and Sodickson, the disclosure of which is incorporated herein by reference, discloses another attempt to minimize the problems caused by scattering in an inhomogeneous sample. The apparatus and method shown in this patent require that the illuminating and/or detected radiation is from a limited solid angle, thereby excluding scattered radiation. This is the opposite approach to the Dähne patent, which includes all the scattered radiation as well as the non-scattered. However, even using this approach, the inhomogeneous nature of the sample may be a problem. Further, by limiting the solid angle from which radiation is used to illuminate the sample or from which the sample radiation is collected, the amount of radiation which can be detected is reduced. This is a particular problem with measurements of glucose, since it is a trace constituent rather than a major constituent of blood, and the amount of signal needed should be maximized, not minimized.

Thus, the inhomogeneities of samples cause serious problems in measurement. It is important, however, to be able to make measurements under these conditions. For example, many diabetics need to take glucose measurements numerous times during the day. Some form of continuous glucose monitor, particularly one that is not bulky, would provide significant benefits to these patients but none is presently available. Thus, a wearable device to measure glucose would be advantageous.

Accordingly, an object of the invention is to provide an apparatus and method for reducing sources of variance in measurement of an inhomogeneous sample.

Another object of the invention is to provide a method and apparatus with reduced bulk for measuring constituents of a sample such as glucose.

A further object of the invention is to provide a device which can measure concentration of optical properties of a solution or sample which is inhomogeneous.

These and other objects and features of the invention will be apparent from the following description and the drawing.

SUMMARY OF THE INVENTION

The invention features a method and apparatus for minimizing the temporal and spatial variations in optical pathlengths in an inhomogeneous sample. The invention uses a reflective enclosure about the sample that allows multipassing of the radiation through the sample prior to detection. In addition, stray ambient light and optical shunting are minimized. The reflective enclosure may act as a specular reflector, diffuse reflector, or both.

As noted, the sources of the inhomogeneity and problems in sample measurement are numerous. First, there is spatial non-uniformity of the sample which can produce variability. For example, this variability occurs when different measurement channels each receive radiation from a different portion of the non-uniform sample. Another source of variability is produced by involuntary relative motion between the source and the sample and/or the sample and the detector. Efforts to eliminate this type of motion by clamping the finger or earlobe are not satisfactory since they tend to deform the finger and thus modify the circulation in a non-repeatable, irreproducible way, leading to measurement uncertainty. This can vary the pathlength, the amount of sample in the area of measurement, or even the water content along the pathlength. Since any of these can affect the measurement, eliminating these sources of variance is helpful.

The method and apparatus for minimizing the variation in optical pathlengths includes a source of illuminating radiation for illuminating the sample. In some circumstances, a plurality of radiation sources is used. Preferably, at least one illumination source is located within the reflective enclosure and if two or more distinct radiation sources are used, they may be located either axially or radially relative to the axis of the sample. Preferred radiation sources include miniature incandescent lamps. The illuminating radiation sources are normally arranged adjacent to a reflective enclosure that at least partially encloses the sample, but a small gap from the reflective enclosure may be used. While a reflective enclosure that totally encloses the sample is preferable, this is not always necessary or even practical because of heat and other constraints.

The sample is illuminated with radiation from the illumination source and the radiation emerging from the sample is detected using a detector. The detector may consist of a plurality of detector units and, preferably, at least one of the detector units is located within the reflective enclosure. In certain circumstances, however, this is not possible, so the reflective enclosure may only partially enclose the sample (e.g., a finger), in a radial direction, preferably with the opening being slightly less than the width of the sample. If a finger or other body part is used as the sample, the apparatus may be used for non-invasive in vivo testing of a bodily fluid. The preferred system totally encloses the finger in a radial direction and both the illumination sources and the detectors are then within the reflective enclosure and adjacent to the finger.

The apparatus and method may also be used with an inhomogeneous fluid as a flow through device. The reflective enclosure may be in the form of a cylinder open at both ends which encloses the sample and a fluid sample may flow through the cylinder during the time of illumination and detection of radiation.

DETAILED DESCRIPTION OF THE DRAWINGS

Figure 1:
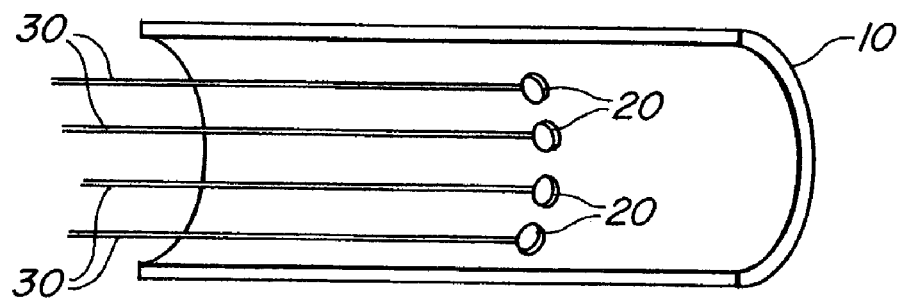
FIG. 1 shows the reflective enclosure and illumination sources for the device which could be used to partially enclose a finger.

The methods and apparatus of the present invention cure some of the problems associated with inhomogeneous samples, particularly as they apply to non-invasive in vivo testing. The methods are applicable to situations where there is spatial inhomogeneity of a sample, differences in pathlength, problems with stray ambient light, and problems with shunted light. The apparatus provides more efficient collection of light from sources and eliminates the need for a significant number of the optical transfer elements such as lens, mirrors and fiber optics, thus allowing easier portability of the device.

Many samples, such as a finger, earlobe or other body part used for non-invasive in vivo testing for glucose, hemoglobin, or other bodily fluid constituents, have problems in reproducibility and sensitivity caused by inherent inhomogeneity in the samples. For example, to determine the glucose level in blood in a finger optically, one must have the illuminating radiation go through the skin layer, bone, blood vessels, the blood itself, and additional water filled tissue. While a number of methods have been tried to ameliorate the problems caused with this type of inhomogeneous sample, none have been totally satisfactory. If a sample is illuminated with radiation and the radiation transmitted, reflected or transflected from the sample is utilized, there are problems with making sure that the pathlength is equal for each detector/illumination source pair and that the detector (or detectors) is obtaining radiation from the identical part of the sample. If not, then any spatial variations in homogeneity of the sample can be a possible source of error. In addition, relative movement between the sample and illumination sources or the sample and the detector is another source of error. Attempts have been made to ameliorate the problems caused by the former using structural restrictions such as the congruent illumination and congruent sampling described in U.S. Pat. Nos. 5,424,545 and 5,434,412. Similarly, attempts to cure the latter problems include clamping or taping of the light source and detector to the sample; none of these have been successful, so a better method is needed.

The present invention uses a reflective enclosure (i.e., a spiegelraum) to enclose the sample under investigation. This reflective enclosure may provide specular or diffuse reflectivity, or both. Materials such as magnesium oxide or even Teflon® may be used to form the reflective material. At least one illumination source and, preferably, the detector, is contained within this reflective enclosure. Using this reflective enclosure and the internal illumination and detection sources, the light illuminating the sample is reflected back and forth multiple times through the sample before hitting the detector. Thus, multipasses through the sample are utilized, thereby averaging the pathlength despite the inherent inhomogeneities. The actual pathlength itself becomes unimportant using this device because the emerging light is "homogenized" by multiple passes through the sample. The light that emerges from the sample and reaches the detector does not meet any of the traditional categories; it is not truly transmitted, reflected or transflected since it is likely to have had multiple passes through the sample. Using this type of multipass system increases the efficiency of the collection of the light from the sources that are included within the reflecting enclosure while eliminating stray ambient light. Further, by including the illumination sources and detection sources within the reflective enclosure, the need for optical transfer elements such as lenses, mirrors and fiber optics is eliminated. While it is preferable that the reflective enclosure completely encircles the sample, in some circumstances it is possible to have a partial enclosure which provides many of the benefits of the present invention while eliminating many of the problems of the prior art. In this case, the detector is normally located at the opening.

FIG. 1 shows a reflective enclosure 10 of the type used to partially enclose a sample such as a finger. Reflective enclosure 10 is made of material that has a reflective coating on its inner side, such as a reflective tape, and preferably is sufficiently flexible to mold to the shape of the sample such as a finger. Aluminum tape is a preferred material for reflective enclosure 10.

FIG. 1 shows a series of illumination sources 20 that are contained within the reflective enclosure 10. Although illumination sources 20 are shown as being distributed radially, they could be distributed along the long axis of reflective enclosure 10. Each of illumination sources 20 has shown having leads 30 attached thereto. While these leads are shown as being inside reflective enclosure 10, it is also possible that a port is used for each of the illumination sources 20 so that the leads are on the outside of reflective enclosure 10. If the leads are inside reflective enclosure 10, it may be preferable to wrap the leads in reflective tape or have a reflective coating on the leads so they do not absorb any light.

Figure 2:
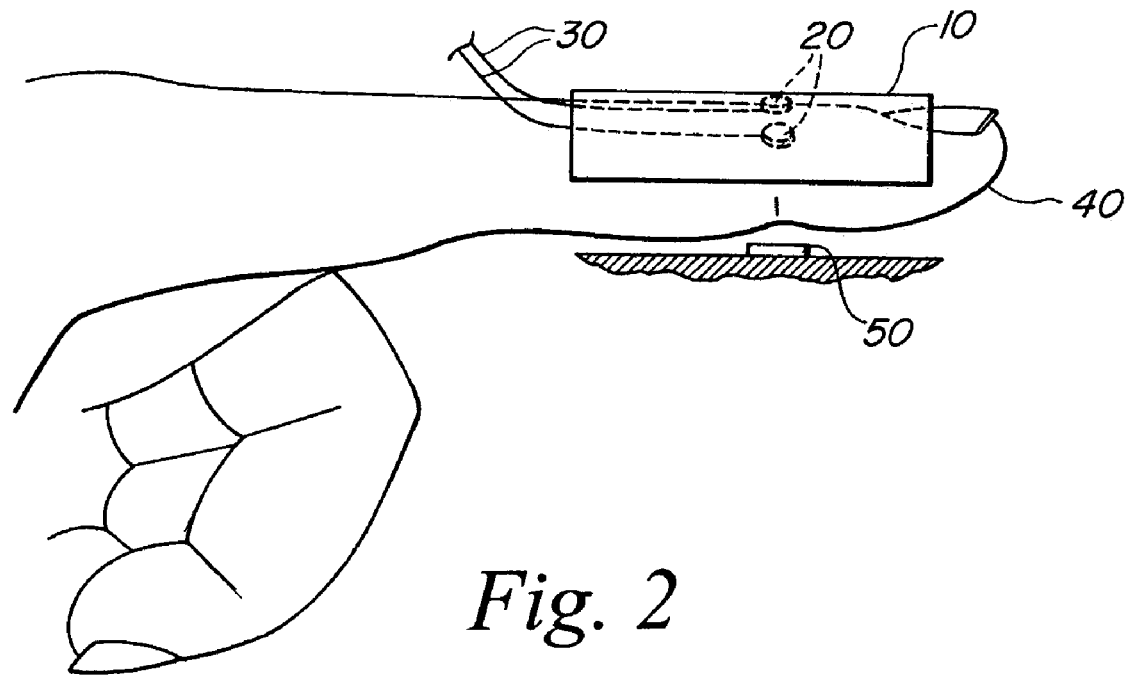
FIG. 2 shows the device of FIG. 1 about a finger, showing the location of the illumination sources at the knuckle.

FIG. 2 shows the reflective enclosure 10 of FIG. 1 about a finger 40. As can be seen from this Figure, reflective enclosure 10 need not completely surround finger 40 but rather there is a gap at one side of finger 40. A detector 50, possibly made up of a plurality of detector units (not shown), is placed at the gap in reflective enclosure 10. This is particularly useful if detector 50 is heat sensitive. By placing detector 50 at the gap, detector 50 is kept at a lower temperature. Many detectors, such as Indium Gallium Arsenide detectors, have some temperature dependence in their noise and responsivity characteristics. As is shown in Example 1, taping the reflective enclosure 10 about the finger 40 to limit the gap to finger width helps eliminate ambient light and prevents shunting, thus yielding more reproducible values.

Figure 3:
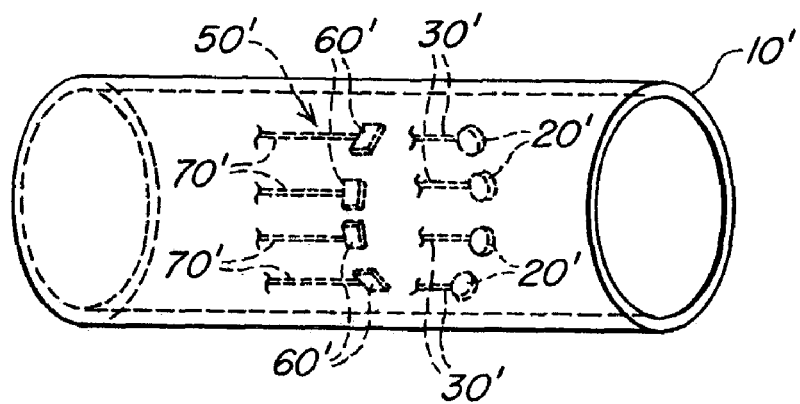
FIG. 3 shows a totally enclosing reflective enclosure having both illumination sources and detectors.

FIG. 3 shows a reflective enclosure 10' which is adapted to completely encircle a finger. As with reflective enclosure 10 in FIG. 1, reflective enclosure 10' can be made of any reflective material, with aluminum tape being a preferred material. A plurality of illumination sources 20', connected to leads 30' are shown, as are a plurality of detector units 60', which make up detector 50'. Detector units 60' are attached to leads 70'. Both illumination sources 20' and detector units 60' are shown as being enclosed within reflective enclosure 10'. Although leads 30' and 70' are shown as being within reflective enclosure 10', they can be external to reflective enclosure 10' and pass through ports through reflective enclosure 10'. In addition, although illumination sources 20' and detection units 60' are shown opposing each other, this is not necessary since the light will emerge from the finger in all directions and illumination sources 20' and detector units 60' could be used at various locations within reflective enclosure 10'. The only requirement is that detection units 60' must be baffled or in some way arranged such that they do not receive light either directly from illumination sources 20' or light which is reflected from illumination sources 20' by the interior of reflective enclosure 10' without passing into the finger.

Figure 4:
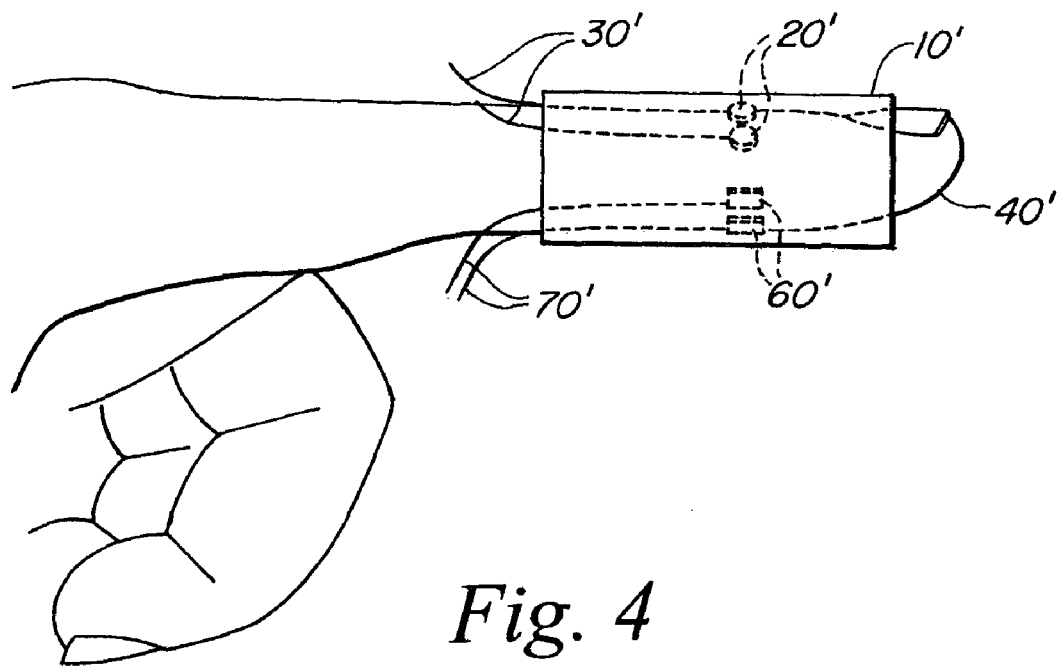
FIG. 4 shows the device of FIG. 3 about a finger as it would be used in operation.

FIG. 4 shows the reflective enclosure 10' of FIG. 3 about a finger 40'. As described in connection with FIG. 2, if the leads 30' and 70' pass within reflective enclosure 10', it is preferable that they be wrapped in a reflective coating.

Both FIG. 2 and FIG. 4 show the illumination sources and detectors as being next to knuckle. This is an important advantage of the present invention; because multiple paths are used, the area of the knuckle, which is less susceptible to deformation, may be used. In other devices, the knuckle would be avoided because it is more opaque a measurement site than other sites. It is the optical efficiency of the present system, with the multipasses through the finger that allow the knuckle to be used.

The following Example shows the benefit of the present invention.

EXAMPLE

In this Example, the effects of using the reflective enclosure and varying the size of the opening were tested. Two micro-lamps, Gilway Part No. 7151, were used as illumination sources. The lamps were set in parallel, touching each other and were oriented transversely to the long axis of the finger at the distal joint. These lamps provided broad spectrum illumination. The finger circumference was approximately 50 mm±1 mm. The following Table shows the values from detectors at four wavelengths in a variety of different enclosure formulations;

The light sources provided illumination across this whole region of wavelengths.

|  | 1254 | 1655 | 1300 | 1378 |
|---|---|---|---|---|
| Black tape, 15 mm wide | 620 | 12 | 1600 | 420 |
| A1 tape, 15 mm wide | 1910 | 22 | 2550 | 1020 |
| Spiegelraum, 5 mm open | 420 | 7 | 660 | 370 |
| Spiegelraum, 10 mm open | 1090 | 13 | 1670 | 670 |
| Spiegelraum, 25 mm open | 2990 | 27 | 3220 | 1230 |
| Spiegelraum, 25 mm open w/tape | 1420 | 15 | 2010 | 710 |

Four detectors were used, filtered to pass various wavelengths. Indium Gallium Arsenide detectors (Hamamatsu G 8370), each with its own distinct broadband filter centered about 1254, 1655, 1300 or 1378 nm, were used to produce the readings for each channel.

Rows 1 and 2 on the Table show the effect of putting a reflector behind the illumination sources. In row 1, black tape, 15 mm wide, was used behind the light sources in lieu of a reflective surface, while row 2 shows the effect of the reflective aluminum tape in lieu of the black absorbing background. Neither of these tapes is wrapped around the finger; they are merely backing for the sources. In all cases, the detectors were spread out in the gap on the opposite side of the finger from the illumination source. As can be seen from the first two rows, using the reflective tape in lieu of the black tape clearly increases the signal at all of the wavelengths.

The third and fourth rows of the Table show a spiegelraum or an enclosure of reflective material about the finger. In these cases, there were 5 mm and 10 mm openings where the detectors were located. Since the values for the 10 mm opening are roughly double the values of the 5 mm opening, this shows that the light leaving the reflective enclosure is substantially uniform. However, the value from the fifth row should be only about 1½ times the amount of the fourth row since the width at the finger joint is approximately 16 mm (16/10≈1½). Instead, the values are much higher than that of the 10 mm opening, suggesting that shunting, or light going around the finger, is occurring. In the fifth row, the edges of the opening were not taped. The sixth row confirms that shunting was occurring. With the edges of the 25 mm opening taped, the values are much closer to that of the 10 mm opening. This suggests that the optimum width for an opening (if used) would be the width of the flat portion of the joint, which is about 13–16 mm. It also suggests that arranging the illumination sources along the axis of the finger rather than radially is likely to provide a higher signal.

One of the problems with using a reflective enclosure that completely encloses the finger is heat. Most detector units are not operable, or have inconsistent readings, at body temperature or higher, so a gap or opening is necessary to protect the detector units. If detector units that can withstand the temperature are available, then these could be used inside the total enclosure.

In lieu of the flexible, cylindrical enclosure such as one made with aluminum tape, an integrating sphere could be used. The sample could be enclosed within the integrating sphere and the illumination source and the detectors could also be enclosed.

The present system may be used with any type of calculations for optical measurement systems. Thus, it is equally applicable to classical spectroscopic measurements and Kromoscopic measurements such as are described in the previously cited patents. The ability to eliminate pathlength problems and increase signal, thus yielding a higher signal to background ratio, is a universal benefit. In addition, since light from all directions is used to illuminate the sample, higher levels of emerging radiation are obtained. It also appears that the light emerging from he sample is more homogeneous that that from normal systems.

Those skilled in the art may appreciate the other advantages and uses of the subject matter disclosed herein. Such other advantages, uses and embodiments of the apparatus and methods described herein are included in the following claims.

What is claimed is:

1. A method of minimizing the variations in optical pathlengths in a testing apparatus comprising the steps of
providing a source of illuminating radiation for illuminating a sample, said illuminating source being in the form of one or more radiation sources;
arranging said illumination source adjacent to a reflective enclosure that at least partially encloses said sample in a radial direction with no more than a single opening in the radial direction, any opening in said reflective enclosure being substantially equal or smaller in size than the width of said sample, and at least one of said radiation sources being located within said reflective enclosure;
illuminating said sample with radiation from said illumination source; and
detecting radiation emerging from said sample with a detector.

2. The method of claim 1 wherein said source of illuminating radiation comprises a plurality of radiation sources.

3. The method of claim 2 where at least two of said radiation sources are located within said reflective enclosure and said radiation sources are located radially relative to said sample.

4. The method of claim 2 where at least two of said radiation sources are located within said reflective enclosure and said radiation source are located axially relative to said sample.

5. The method of claim 2 wherein said radiation sources comprise miniature incandescent lamps.

6. The method of claim 2 wherein said detector comprises a plurality of detector units.

7. The method of claim 1 wherein said reflective enclosure comprises a cylinder open at both axial ends.

8. The method of claim 7 wherein said cylinder encloses said sample.

9. The method of claim 8 wherein said sample is a fluid.

10. The method of claim 9 wherein said fluid flows through said cylinder during time of illumination and detection of radiation.

11. The method of claim 1 wherein said sample contains a bodily fluid.

12. The method of claim 11 wherein said testing apparatus is adapted for in vivo non-invasive testing of a material carried in said bodily fluid.

13. The method of claim 12 wherein said sample is a finger that is illuminated and from which said radiation is detected.

14. The method of claim 12 wherein said reflective enclosure only partially encloses said sample in a radial direction, with an opening approximately equal in size to the width of said sample.

15. The method of claim 12 wherein said reflective enclosure totally encloses said sample in a radial direction, and wherein said enclosure comprises said illumination source and said detector within said enclosure.

16. The method of claim 13 wherein said portion of said finger that is illuminated and from which said radiation is detected is a knuckle.

17. A testing apparatus for simulating sample homogeneity comprising:
a source of illuminating radiation for illuminating a sample, said illumination source being arranged adjacent to a reflective enclosure that at last partially encloses said sample in a radial direction with no more than a single opening in a radial direction, any opening in said reflective enclosure being substantially equal or smaller in size than the width of said sample, and said source of illuminating radiation being in the form of one or more radiation sources, at least one of said radiation sources being located within said reflective enclosure; and
a detector for detecting radiation emerging from said sample.

18. The apparatus of claim 17 wherein said source of illuminating radiation comprises a plurality of radiation sources.

19. The apparatus of claim 18 where at least two of said radiation sources are located within said reflective enclosure and said radiation sources are located radially relative to said sample.

20. The apparatus of claim 18 where at least two of said radiation sources are located within said reflective enclosure and said radiation sources are located axially relative to said sample.

21. The apparatus of claim 18 wherein said radiation sources comprise miniature incandescent lamps.

22. The apparatus of claim 17 wherein said detector comprises a plurality of detector units.

23. The apparatus of claim 17 wherein said reflective enclosure comprises a cylinder open at both axial ends.

24. The apparatus of claim 23 wherein said cylinder encloses said sample.

25. The apparatus of claim 18 wherein said sample is contained in a fluid.

26. The apparatus of claim 25 wherein said testing apparatus is adapted for in vivo non-invasive testing of a material carried in bodily fluid.

27. The apparatus of claim 26 wherein said reflective enclosure is designed to at least partially enclose a finger.

28. The apparatus of claim 26 wherein said reflective enclosure only partially encloses said sample in a radial direction, with an opening approximately equal in size to the width of said sample.

29. The apparatus of claim 26 wherein said reflective enclosure totally encloses said sample in a radial direction, and wherein said enclosure comprises said illumination source and said detector within said enclosure.

30. The apparatus of claim 27 wherein said portion of said finger that is illuminated and from which said radiation is detected is a knuckle.

* * * * *